United States Patent [19]

Meisner

[11] Patent Number: 4,590,067
[45] Date of Patent: May 20, 1986

[54] TREATMENT FOR PERIODONTAL DISEASE

[75] Inventor: Lorraine F. Meisner, Madison, Wis.

[73] Assignee: Peritain, Ltd., Madison, Wis.

[21] Appl. No.: 662,069

[22] Filed: Oct. 18, 1984

[51] Int. Cl.⁴ .......................... A61K 7/16; A61K 7/22
[52] U.S. Cl. ........................................ 424/54; 424/49;
514/900; 514/902
[58] Field of Search .................. 514/900, 902; 424/49, 424/54

[56] References Cited

U.S. PATENT DOCUMENTS

| | | | |
|---|---|---|---|
| 3,689,636 | 9/1972 | Svajda | 424/49 |
| 3,886,265 | 5/1975 | Evers et al. | 424/49 |
| 4,029,760 | 6/1977 | DeRoeckborntto | 424/48 |
| 4,254,101 | 3/1981 | Denny, Jr. | 424/52 |
| 4,339,431 | 7/1982 | Gaffar | 424/54 |
| 4,405,610 | 9/1983 | Krnjevic | 514/902 |
| 4,477,428 | 10/1984 | Silbering et al. | 424/54 |
| 4,515,771 | 5/1985 | Fine | 424/54 |

OTHER PUBLICATIONS

Chem. Abst. 77: 73943j (1972)–Gustafson et al.
Tapadinhas, et al., *Pharmatherapeutica*, 3(3), 157–168 (1982).
Bekesi, et al., *Cancer Research*, 29, 353–359 (1969).
Laszlo, et al., *J. of the National Cancer Institute*, 24, 267–281.
El-Ashiry, et al., *Int. Zeit. Vitaminforschung*, 34, 202–218 (1964).
Litwin, *J. Cell Science*, 14, 671–680 (1974).
Jain, et al., *Agents and Actions*, 11(3) 243–249 (1981).
Gualano, et al., *Pharmacology Res. Commun.*, 1983 Jul., 15(7), 683–696.
Thomas, et al., *J. Pharm. and Pharmacol*, Feb. 1974, 26(2), 151–152.
Borne et al., *J. Med. Chem.*, Dec. 1972, 15(12), 1325–1326.
Hall, et al., *J. Pharm.*, Dec. 1980, 69(12), 1451–1452.
Kwapiszewski, et al., *Arch. Immunol. Ther. Exp.* (Warsz), 1979, 17(6), 729–731.

*Primary Examiner*—Douglas W. Robinson
*Attorney, Agent, or Firm*—Barnes & Thornburg

[57] ABSTRACT

A composition for preventing and treating periodontal disease, comprising bone meal, ascorbic acid, tyrosine, and either glucosamine or cysteine.

15 Claims, No Drawings

TREATMENT FOR PERIODONTAL DISEASE

The present invention relates to periodontal disease, and more particularly to the prevention, treatment, and amelioration thereof, employing a novel combination of natural substances for such purpose.

Periodontal disease is an inflammatory disorder of the gums variously referred to as gum disease, periodontitis, and gingivitis. Since the time that fluoride came into widespread use in drinking water and toothpaste to help reduce tooth loss due to decay, gum disease has become the largest cause of tooth loss in the adult population of the United States, accounting for approximately 70% of such losses. The disorder results from the accumulation of plaque, particularly within the gum line, which, unless effectively removed, produces a chronic inflammatory process of the gingiva that spreads and destroys the tissues supporting the tooth as well as the tooth itself. Effective removal of plaque is difficult, even with a vigorous and sustained program of brushing and flossing, and it has become clear that for effective control of periodontal disease, a more specific treating agent is needed.

It is therefore an object of this invention to provide a method and means for preventing and treating periodontal disease.

Another object is to provide a combination of natural substances useful for preventing and ameliorating the effects of periodontal disease.

Other objects of the invention and its advantages over the prior art will be apparent from the following description and claims.

In accordancw with the invention, a powder base is provided having the following composition for the treatment of existing periodontal disease:

| Parts by Weight | Component |
| --- | --- |
| 2 to 10 | Bone meal or similar calcium source; |
| 1 to 5 | Glucosamine or other simple sugar; or amino sugar having anti-inflammatory activity |
| 1 to 5 | Ascorbic acid |
| 0.5 to 2.5 | Tyrosine, phenylalanine, or other precursor or stimulant of epinephrine or nor-epinephrine production |

Bone meal, or the equivalent, serves as a source of calcium for tooth regeneration, as a gentle cleansing agent, and as a filler. Equivalent substances include calcium gluconate, calcium carbonate, tricalcium phosphate, dolomite, and the like.

Glucosamine, preferably used in the form of the salt with hydrochloric, sulfuric, phosphoric, or other biocompatible acid, is known to have an anti-inflammatory effect when taken orally. Tapadinhas et al, *Pharmatherapeutica*, 3(3), 157-168 (1982). Other sugars and sugar derivatives of similar activity include 2-deoxy-D-glucose, 2-deoxy-D-galactose, mannose, D-mannosamine, D-galactosamine, and the like. Bekesi et al, *Cancer Research*, 29, 353-359 (1969); Laszlo et al., *J. Natl. Cancer Inst.*, 24, 267-281 (1960); Bekesi et al, *J. Clinical Chem.*, 211, 3766-72 (1969). Also useful are glucosamine-6-phosphate, N-acetyl-D-glucosamine, N-acetyl-D-galactosamine, uridine diphosphate (UDP) glucose, UDP-N-acetylglucosamine, and the like.

Ascorbic acid is the only ingredient in the above formulation which is disclosed in the scientific literature as having been used in the treatment of periodontal disease. A study reported in 1964 showed that oral ingestion of ascorbic acid, combined with scaling of calculus from the periodontal disease sites, gave a greater increase in tooth stability than either treatment alone, both of which showed a small beneficial effect. El-Ashiry et al, *Int. Zeit. Vitaminforschung*, 34, 202-18 (1964). Prior to the present invention, however, ascorbic acid has never been used topically on gums, either alone or in any combination with other substances.

As a precursor of epinephrine, tyrosine is a preferred substance for use in the present invention, because it has been shown in tissue culture to promote proliferation of the type of cell (fibroblasts) which are involved in the healing of periodontal tissue. Litwin, *J. Cell Science*, 14, 671-80 (1974). Activity of this sort is exhibited by both epinephrine and nor-epinephrine, and consequently by precursors and stimulants of epinephrine and nor-epinephrine synthesis.

The composition described above is effective for the treatment and alleviation of peridontal disease. For preventing the disease or, after treatment has relieved the inflammatory condition which characterizes the disease, the composition is suitably modified by replacing the glucosamine or other anti-inflammatory sugar or amino sugar with an amino acid having an anti-inflammatory effect. For this purpose, cysteine is preferred because it is bactericidal against *Streptococcus mutans* in addition to being anti-inflammatory in action. Other suitable amino acids include creatine, creatinine, L-tryptophan, valine, alanine, glycine, glutamine, aspartic acid, and S-methylcysteine, as well as the esters, N-benzenesulfonyl derivatives, and diazomethyl ketone and chloromethyl ketone analogs of the N-tosyl derivatives thereof, and the like. Jain et al, *Agents and Actions*, 11, 3 (1981); Gualano et al, *Pharmacol. Res. Commun.*, 1983 Jul., 15(7), p. 683-96; Thomas et al, *J. Pharmacol.*, Feb. 74, 26(2), p. 151-2; Borne et al, *J. Med. Chem.*, Dec. 72, 15(12), p. 1325-6; Hall et al, *J. Pharm. Sci.*, 1980 Dec., 69(12), p. 1451-2; Kwapiszewski et al, *Arch. Immunol. Ther. Exp.* (Warsz.), 1979, 27(6), p. 729-31.

In addition to the above ingredients, which are directed toward the primary purpose of the present invention, the novel composition may include certain optional ingredients, such as fluoride ion sources, sudsing agents, flavoring agents, sweeting agents, anticalculus agents, antiplaque agents, coloring agents, opacifying agents, and the like, as described in Denny U.S. Pat. No. 4,254,101, which is incorporated herein by reference.

The composition of the present invention, when prepared in the form of a powder, can be used by lightly applying with a soft toothbrush into the gingival-tooth junction twice a day, followed, if desired, by rinsing. It can also be used in the form of a paste or gel, in which the total concentration can be as low as around 5% by weight. For use in treating periodontal disease, the powder form is advantageously used, without dilution. The preventive formulation without glucosamine can be used as a "matrix," blown in with a periojet at the time of surgery to promote healing and also to provide a better attachment for tissue.

The composition of the invention can be formulated as a toothpaste or a gel by milling in a conventional manner with an appropriate amount of glycerol, sorbitol, and water, plus a thickening agent (for example, xanthan gum) to produce the desired consistency, plus an opacifying agent if the toothpaste form is desired.

These formulations are used in a conventional manner, with care to work the material into the gingival-tooth junction.

The following examples are representative of powders, gels, and toothpastes embodying the novel compositions of the present invention. All proportions are in percent by weight.

EXAMPLE 1

| Powder formulation: | |
| --- | --- |
| Bone meal | 44% |
| Glucosamine | 22% |
| Ascorbic acid | 22% |
| Tyrosine | 12% |
| | 100% |

EXAMPLE 2

| Powder formulation: | |
| --- | --- |
| Calcium gluconate | 40% |
| Mannose | 25% |
| Ascorbic acid | 20% |
| Phenylalanine | 15% |
| | 100% |

EXAMPLE 3

| Powder formulation: | |
| --- | --- |
| Bone meal | 45% |
| Cysteine | 20 |
| Ascorbic acid | 23 |
| Tyrosine | 12 |
| | 100% |

EXAMPLE 4

| Gel formulation: | |
| --- | --- |
| Powder, Example 1 | 6% |
| Sorbitol (70% aqueous) | 64 |
| Glycerol | 23 |
| Xanthan gum | 0.25 |
| Carboxyvinyl polymer | 0.25 |
| Sodium dodecyl sulfate | 1.5 |
| Flavor, q.s. | |
| Color, q.s. | |
| Water | 5 |
| Phosphate buffer to pH 7 | |
| | 100% |

EXAMPLE 5

| Toothpaste formulation: | |
| --- | --- |
| Powder, Example 1 | 20% |
| Sorbitol (70% aqueous) | 42.5 |
| Precipitated silica | 17 |
| Glycerol | 15 |
| Xanthan gum | 0.25 |
| Carboxyvinyl polymer | 0.25 |
| Sodium dodecyl sulfate | 1.0 |
| Flavor, q.s. | |
| Water | 4.0 |
| Phosphate buffer to pH 7 | |
| | 100% |

The following example reports the results of a clinical study of a composition of the present invention in the treatment of advanced periodontal disease.

EXAMPLE 6

The patients in this study had all been referred for periodontal surgery because of advanced disease. Selection for the study was conditioned on two factors: (1) no immediate necessity for the surgery; and (2) willingness to learn to use the required brushing technique., as described in the publication "The Realistic Way to Dental Wellness," by John H. Duffy, D.D.S., Realistic Hygiene, Inc., 2354 Highway AB, McFarland, Wisc. 53558, U.S.A. (1978). Parallel groups of controls and test patients were selected on the basis of being as clinically similar as possible. As exceptions, two patients were chosen who had earlier refused to have surgery and had been "dry" brushing (without dentifrice or any other material added to the mouth) with proper technique under periodontal supervison for eighteen months and two years, respectively, without much impact on their disease. These two patients were chosen as test patients to study the beneficial effects of brushing alone as compared with short-term use of the powder of the present invention.

Both control and test patients practiced "dry" brushing for a minimum of three weeks to assure that they were using the proper brushing techniques, acceptable to the periodontist conducting the study. After the initial period, in which brushing techniques were evaluated and mistakes corrected, the controls were instructed to continue brushing twice a day, while the test patients were told to brush twice daily using a powder having the following composition:

| Bone meal | 4.6 | parts by weight |
| --- | --- | --- |
| Glucosamine | 2.8 | |
| Ascorbic acid | 3.2 | |
| Tyrosine | 1 | |

Progress was measured by using a University of Michigan periodontal probe to measure any difference in "pocket" depth from the beginning of the study until its conclusion. The "pocket" is the space between gum and tooth in periodontal disease which does not exist in healthy gums, providing a site for bacterial infection and inflammation which destroys the surrounding gum and osseous support for the tooth, and eventually causes the tooth itself to be lost. Pocket depth measurements were made on four sides of each tooth. All four readings for each tooth were then added together for all of the teeth of a given patient, and the result was divided by the total number of the patient's teeth (varying from patient to patient) to give an average score per tooth for the sum of the pocket depths on the four sides. A decrease in average pocket depth thus would represent an improvement in the patient's condition and a positive response to the treatment being employed.

Because brushing is a one-handed operation, usually done with the same hand by a given patient, the brushing tends to be more effective on the side opposite the brushing hand, with the result that periodontal disease tends to be less advanced on that side. For the same reason, the treatment carried out in the present invention also tends to by unsymmetrical. Because of this effect, data were accumulated separately for the left and right sides of the patients' mouths in order to rule out any resulting bias in the results.

As the accompanying tables show, there is no consistent relationship between the effects of proper brushing alone and time of brushing, with some patients showing considerable improvement while others showed deterioration. Indeed, in the control group there was not even a good correlation in the results on each side of the mouth, except that the left side averaged a greater improvement, as would be expected since the subjects were right-handed. On the other hand, in the test group no patient got worse, and the average decrease in pocket depth was approximately tenfold that seen with brushing alone. In addition, slightly greater improvement was seen on the right side, suggesting that the powder had compensated for the effects of unequal brushing.

During the course of this trial, all patients were evaluated at frequent intervals (every three weeks or so) to make sure that their conditions did not worsen, which would have made immediate surgery necessary.

One patient (MS-C) had already had surgery on the right side of her mouth and wished to delay the surgery on the left side. She was put on the powder; after only one month of brushing with the powder, she improved so dramatically that surgery on the left side may no longer be necessary.

MS(A) was the first patient in the study, and several different proportions of ingredients in the powder were tested on him until an optimum formulation was found, as judged by a maximum suppression of inflammation. This was the formulation thereafter used on MS(A) and adopted for all of the other patients in the study. The time shown below in Tables 3 and 4 for MS(A)'s use of the powder are for his use of the optimum formulation, and, to simplify comparisons, all improvements achieved prior to MS(A)'s use of the final formulation are ascribed (inaccurately to "brushing alone"—i.e., "dry" brushing. Thus, for MS(A), the improvement attributed to four months of brushing alone actually included two months of brushing with powder having varying proportions of ingredients. To avoid this inaccuracy, the results of the study are also reported at the bottom of Tables 3 and 4 without the data from MS(A).

This more critical treatment of the data demonstrates even more impressively the effect of the powder on periodontal disease.

Although the only parameter which could be objectively quantified here was pocket depth, it was noted that the degree of grossly observable inflammation decreased in parallel with the degree of decrease in pocket depth.

In summary, the results of this clinical trial show that the powder formulation employed is effective in the treatment of periodontal disease, either to decrease inflammation prior to surgery or, in some cases, to even replace surgery.

TABLE 1
CONTROLS
Left Side of Mouth

| Subjects | Duration of Brushing (months) | Average Pocket Depth (mm) (Sum, 4 sides per tooth) | | |
|---|---|---|---|---|
| | | Before Brushing | After | Difference |
| JR | 3½ | 13.14 | 13.50 | +0.36 |
| DB | 1¾ | 11.93 | 11.86 | −0.07 |
| DG | 2¼ | 11.76 | 11.15 | −0.61 |
| CM | 2¼ | 13.54 | 13.62 | +0.08 |
| AS | 3¾ | 11.64 | 9.69 | −1.95 |
| SS | 3 | 9.23 | 8.15 | −1.08 |
| RT | 2¾ | 8.27 | 9.00 | +0.73 |
| | | Average | | −0.36 |

TABLE 2
CONTROLS
Right Side of Mouth

| Subjects | Duration of Brushing (months) | Average Pocket Depth (mm) (Sum, 4 sides per tooth) | | |
|---|---|---|---|---|
| | | Before Brushing | After | Difference |
| JR | 3½ | 14.73 | 14.14 | −0.59 |
| DB | 1¾ | 13.33 | 13.75 | +0.42 |
| DG | 2¼ | 13.14 | 13.07 | −0.07 |
| CM | 2¼ | 13.00 | 13.71 | +0.71 |
| AS | 3¾ | 12.50 | 10.50 | −2.00 |
| SS | 3 | 8.92 | 8.00 | −0.92 |
| RT | 2¾ | 9.16 | 9.33 | +0.17 |
| | | Average | | −0.26 |

TABLE 3
TEST PATIENTS
Left Side of Mouth

| Subjects | Duration (months) | | Average Pocket Depth (mm) (Sum, 4 sides per tooth) | | | Difference | | |
|---|---|---|---|---|---|---|---|---|
| | Brushing Alone | Brushing + Powder | Before Any Treatment | After Brushing Alone | After Brushing + Powder | After Brushing Alone | After Brushing + Powder | After Both |
| GG | 1 | 2 | 14.62 | 12.77 | 11.92 | −1.85 | −0.85 | −2.70 |
| NH | 1½ | 2 | 8.89 | 8.07 | 7.43 | −0.82 | −0.64 | −1.46 |
| RM* | 18 | 1½ | 16.43 | 13.57 | 11.57 | −2.86 | −2.00 | −4.86 |
| MR | 1¼ | 2 | 10.00 | 10.89 | 8.64 | +0.89 | −2.25 | −1.36 |
| MS(A) | 4 | 4 | 11.62 | 7.31 | 6.69 | −4.31 | −0.62 | −4.93 |
| MS(B) | 1½ | 2 | 13.66 | 13.50 | 10.43 | −0.16 | −3.07 | −3.23 |
| MS(C) | 5 | 1 | 12.86 | 10.57 | 8.64 | −2.29 | −1.93 | −4.22 |
| MS(D)* | 24 | 1½ | 13.85 | 11.00 | 9.00 | −2.85 | −2.00 | −4.85 |
| | | | | | Average | −1.78 | −1.67 | −3.45 |
| | | | | Average, excluding MS(A) | | −1.42 | −1.82 | −3.24 |

*RM and MS(D), prior to the beginning of this study, had declined surgery and were treated by "dry" brushing for the periods shown. When the composition ("powder") of the present invention became available, their brushing was continued with the powder. The results permit a comparison of the improvement provided by short-term brushing with the powder versus long-term brushing without.

TABLE 4

TEST PATIENTS
Right Side of Mouth

| Subjects | Duration (months) Brushing Alone | Duration (months) Brushing + Powder | Average Pocket Depth (mm) (Sum, 4 sides per tooth) Before Any Treatment | Average Pocket Depth (mm) (Sum, 4 sides per tooth) After Brushing Alone | Average Pocket Depth (mm) (Sum, 4 sides per tooth) After Brushing + Powder | Difference After Brushing Alone | Difference After Brushing + Powder | After Both |
|---|---|---|---|---|---|---|---|---|
| GG | 1 | 2 | 16.15 | 14.85 | 12.77 | −1.30 | −2.08 | −3.38 |
| NH | 1½ | 2 | 10.07 | 8.64 | 7.79 | −1.43 | −0.85 | −2.28 |
| RM* | 18 | 1½ | 14.36 | 12.29 | 10.71 | −2.07 | −1.58 | −3.65 |
| MR | 1¼ | 2 | 11.21 | 11.86 | 8.57 | +0.65 | −3.29 | −2.64 |
| MS(A) | 4 | 4 | 10.92 | 7.25 | 6.25 | −3.67 | −1.00 | −4.67 |
| MS(B) | 1½ | 2 | 14.29 | 14.70 | 11.00 | +0.41 | −3.70 | −3.29 |
| MS(C)** | | | | | | | | |
| MS(D)* | 24 | 1½ | 14.07 | 10.07 | 9.71 | −4.00 | −0.36 | −4.36 |
| Average | | | | | | −1.63 | −1.84 | −3.47 |
| Average, excluding MS(A) | | | | | | −1.29 | −1.98 | −3.27 |

*RM and MS(D), prior to the beginning of this study, had declined surgery and were treated by "dry" brushing for the periods shown. When the composition ("powder") of the present invention became available, their brushing was continued with the powder. The results permit a comparison of the improvement provided by short-term brushing with the powder versus long-term brushing without.

**MS(C) is not included because she had received surgery on the right side of her mouth. Only the left side of the mouth was treated with powder.

What is claimed is:

1. A composition useful in the prevention and treatment of periodontal disease, a disease characterized by a chronic inflammation of gingival tissue leading to destruction of connective tissues surrounding the teeth, which composition comprises the following ingredients, expressed in parts per weight: a calcium source selected from the group consisting of bone meal, calcium gluconate, calcium carbonate, calcium phosphate, and dolomite, 2 to 10 parts; ascorbic acid, 1 to 5 parts; a precursor or stimulant of epinephrine or nor-epinephrine production selected from the group consisting of tyrosine and phenylalanine, 0.5 to 2.5 parts; and an anti-inflammatory substance, 1 to 5 parts, said anti-inflammatory substance being selected from the group consisting of mannose, 2-deoxy-D-glucose, glucosamine, glucosamine-6-phosphate, N-acetylglucosamine, galactosamine, cysteine, glutamine, alanine, L-tryptophan, valine and creatinine.

2. The composition of claim 1 wherein said calcium source is bone meal.

3. The composition of claim 1 wherein said precursor or stimulant is tyrosine.

4. The composition of claim 1 wherein said anti-inflammatory substance is glucosamine.

5. The composition of claim 4 wherein said glucosamine is used in the form of a salt with a biocompatible acid.

6. The composition of claim 1 wherein said anti-inflammatory substance is cysteine.

7. A composition useful in the prevention of periodontal disease which comprises the following ingredients in parts by weight:

| | |
|---|---|
| Bone meal | 2 to 10 |
| Cysteine | 1 to 5 |
| Ascorbic acid | 1 to 5 |
| Tyrosine | 0.5 to 2.5. |

8. A composition useful in the treatment of periodontal disease which comprises the following ingredients in parts by weight:

| | |
|---|---|
| Bone meal | 2 to 10 |
| Glucosamine | 1 to 5 |
| Ascorbic acid | 1 to 5 |
| Tyrosine | 0.5 to 2.5. |

9. A method for preventing or treating periodontal disease, said disease characterized by a tissue destructive inflammation of gingival tissue, which method comprises applying to the gingival-tooth junction a therapeutically effective amount of a composition comprising the following ingredients, expressed in parts by weight: a calcium source selected from the group consisting of bone meal, calcium gluconate, calcium carbonate, calcium phosphate and dolomite, 2 to 10 parts, ascorbic acid, 1 to 5 parts; a precursor or stimulant of epinephrine or non-epinephrine production selected from the group consisting of tyrosine and phenylalanine, 0.5 to 2.5 parts; and an anti-inflammatory substance, 1 to 5 parts, said anti-inflammatory substance being selected from the group consisting of mannose, 2-deoxy-D-glucose, glucosamine, glucosamine-6-phosphate, N-acetylglucosamine, galactosamine, cysteine, glutamine, alanine, L-tryptophan, valine and creatinine.

10. The method of claim 9 wherein the anti-inflammatory substance is selected from the group consisting of glucosamine, glucosamine-6-phosphate, and N-acetyl-D-glucosamine.

11. The method of claim 9 wherein the anti-inflammatory substance is glucosamine.

12. The method of claim 11 wherein the precursor or stimulant is tyrosine.

13. The method of claim 9 wherein the anti-inflammatory substance is cysteine.

14. The method of claim 13 wherein the precursor or stimulant is tyrosine.

15. The method of claim 9 wherein the composition is applied by brushing it into the gingival-tooth junction.

* * * * *